United States Patent [19]

Sinskey et al.

[11] Patent Number: 4,649,119
[45] Date of Patent: Mar. 10, 1987

[54] CLONING SYSTEMS FOR CORYNEBACTERIUM

[75] Inventors: Anthony J. Sinskey, Boston; Graham C. Walker, Arlington, both of Mass.; Kanji Higashio, Saitama, Japan; Eswara A. Rao, Beverly; William G. Shanabruch, Somerville, both of Mass.; Makoto Yoshihama, Saitama, Japan

[73] Assignee: Massachusetts Institute of Technology, Cambridge, Mass.

[21] Appl. No.: 489,298

[22] Filed: Apr. 28, 1983

[51] Int. Cl.[4] .................. C12N 1/00; C12N 15/00; C12P 21/00
[52] U.S. Cl. .................................. 435/317; 435/68; 435/172.3; 435/253; 935/29; 935/72; 935/74
[58] Field of Search ............... 435/172.1, 172.2, 172.3, 435/253, 243, 317, 843, 844, 845, 846, 832, 833, 834–839

[56] References Cited

U.S. PATENT DOCUMENTS

| | | | |
|---|---|---|---|
| 4,343,906 | 8/1982 | Reusser et al. | 435/253 |
| 4,493,893 | 1/1985 | Mielenz et al. | 435/172.3 |
| 4,508,827 | 4/1985 | Olsen | 435/253 |
| 4,514,502 | 4/1985 | Miwa et al. | 435/253 |

FOREIGN PATENT DOCUMENTS

| | | | |
|---|---|---|---|
| 0058889 | 1/1982 | European Pat. Off. | 435/172.2 |
| 0063953 | 3/1982 | European Pat. Off. | 435/172.2 |
| 0073062 | 2/1983 | European Pat. Off. | 435/172.2 |

OTHER PUBLICATIONS

Hopwood, D. A., *Ann. Rev. Microbiol.*, 1981, vol. 35, pp. 237–272, "Genetic Studies with Bacterial Protoplasts".
White et al., *Principles of Biochemistry*, McGraw Hill NY, 1968, p. 105, 4th Edition.

*Primary Examiner*—Thomas G. Wiseman
*Assistant Examiner*—Robin Lyn Teskin
*Attorney, Agent, or Firm*—Thomas J. Engellenner; James E. Maslow

[57] ABSTRACT

The invention is a method for obtaining a chimeric plasmid which can serve as a vector for inserting one or more foreign or native genes into Corynebacterium and a second species of bacteria. The plasmid is the ligation product of plasmid DNA from Corynebacterium as well as plasmid DNA from a non-Corynebacterium species of bacteria. Also disclosed is a method for forming protoplasts from Corynebacterium organisms and transforming the protoplasts with vectors, e.g., the chimeric plasmids of the invention.

7 Claims, 6 Drawing Figures

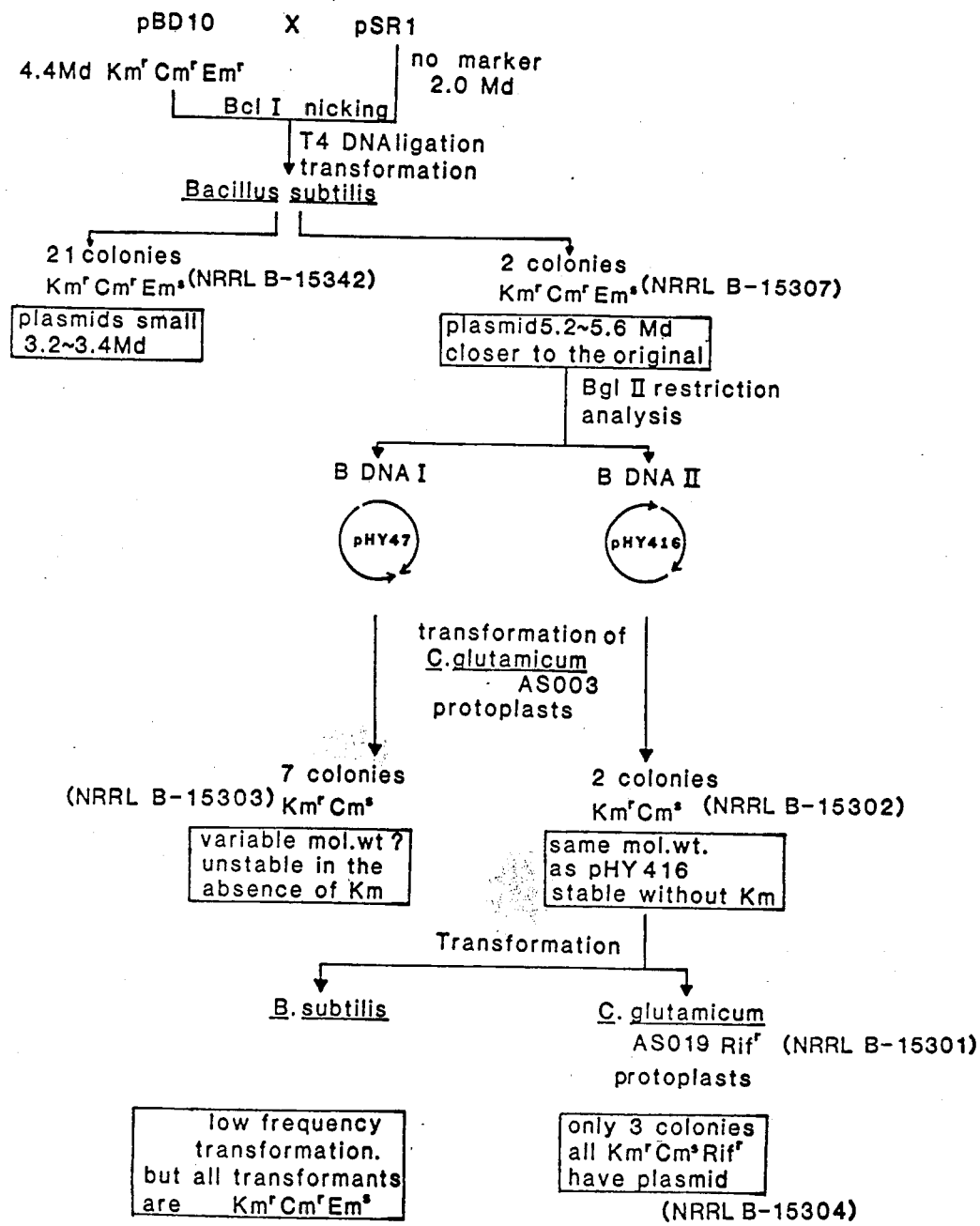
Figure 1. TRANSFORMATION: SEQUENCE & TERMINOLOGY

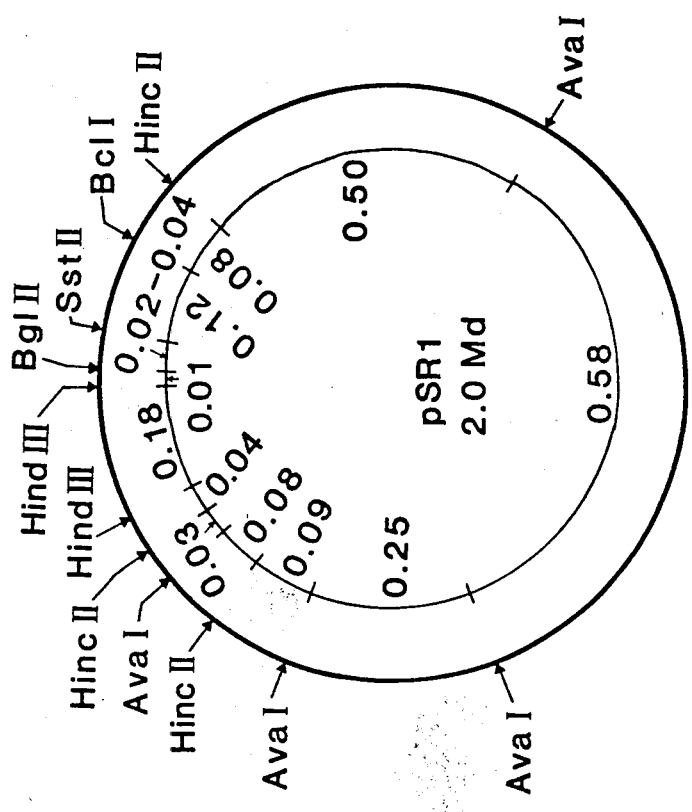
Figure 2. Restriction Map of pSR1

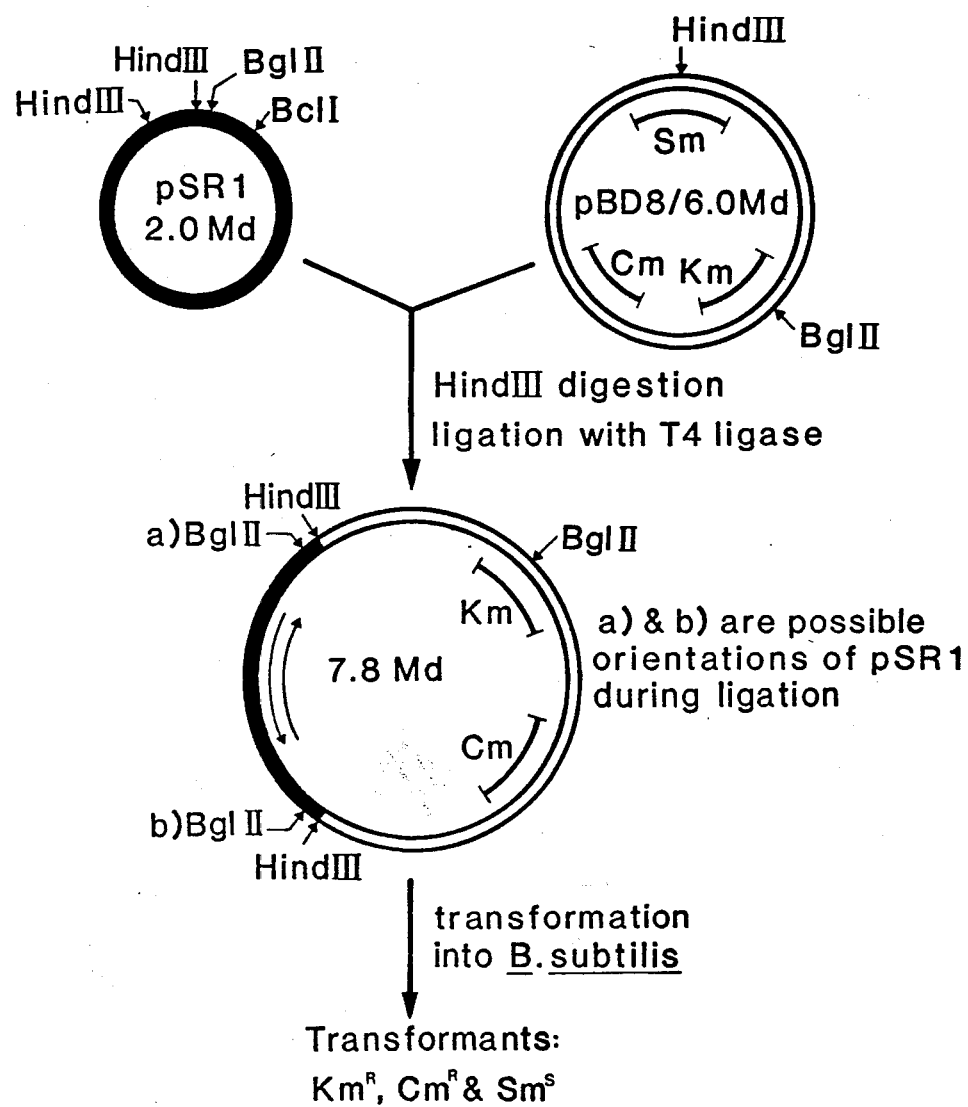

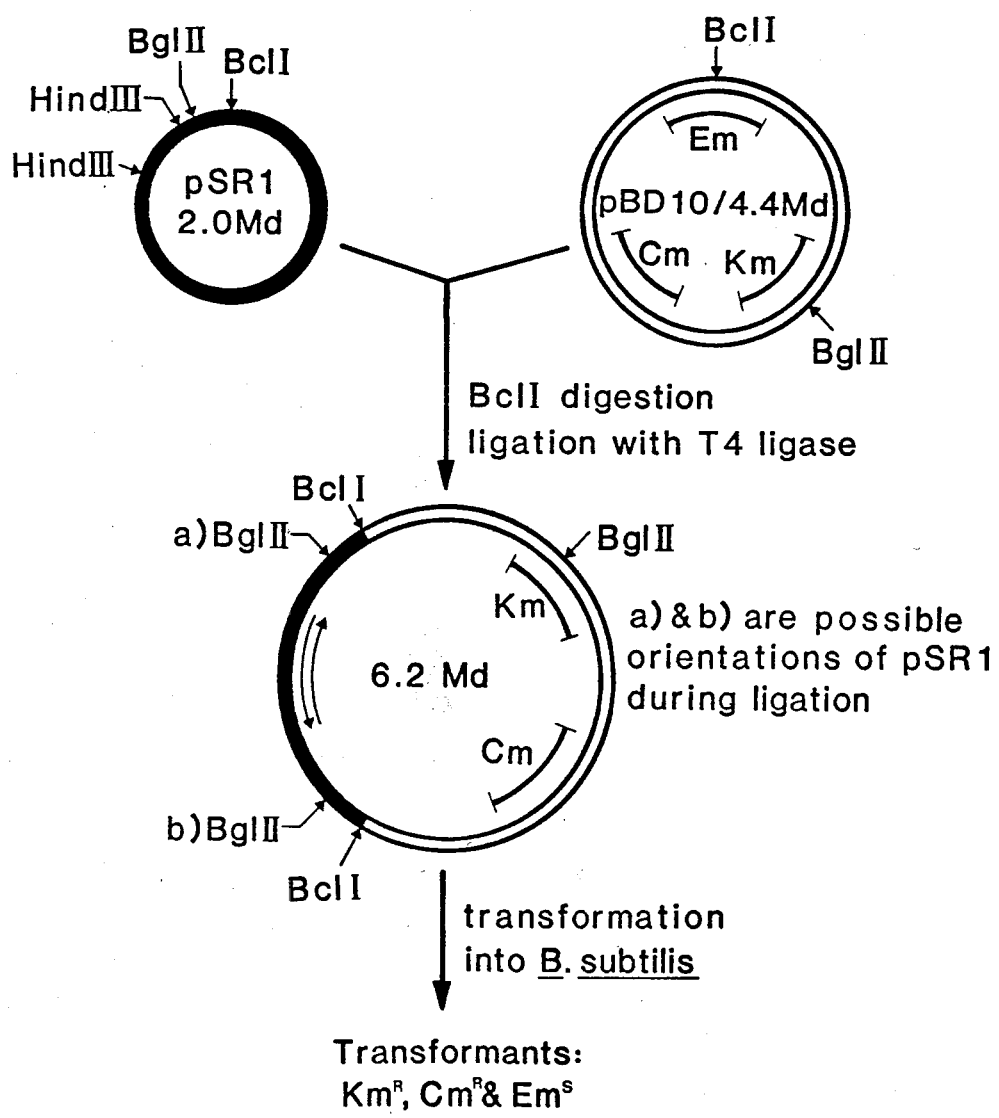
Figure 4. A chimeric plasmid composed of 2.0 Md pSR1 and pBD10 at BclI site

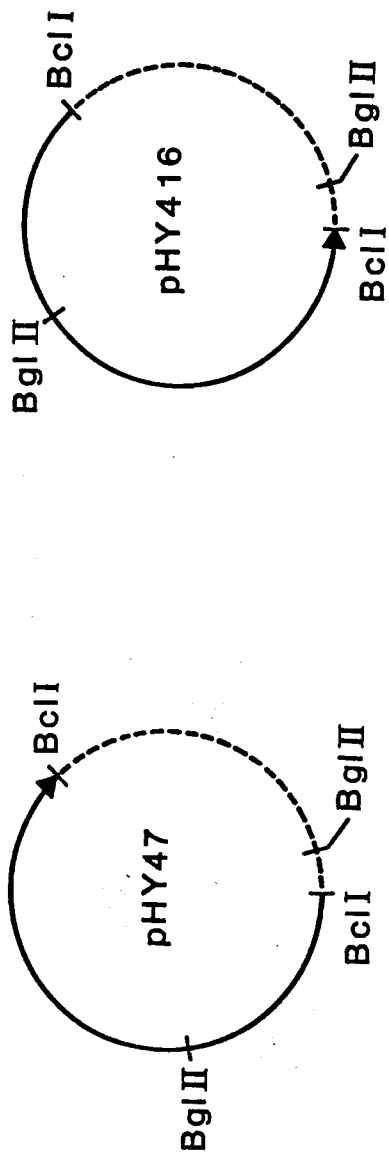

CLONING SYSTEMS FOR CORYNEBACTERIUM

The Government has rights in this invention pursuant to Grant Number NIH-5-T32-CA09258-04 awarded by the U.S. Department of Health and Human Services.

BACKGROUND OF THE INVENTION

Preparation of protoplasts is well known, especially in gram-positive microorganisms. The technology for protoplast formation in both gram-positive and gram-negative microorganisms is discussed extensively by Hopwood, "Genetic Studies with Bacteria Protoplasts," Ann. Rev. Microbiol. 1981. 35: 237-72. The preponderance of techniques discussed by Hopwood related to protoplast formation in Streptomyces and Bacillus organisms. The transformation of protoplasts is described at pages 263-268. Protoplast fusion techniques are reviewed by Peberdy, Enzyme Microb. Technol., 1980, vol. 2, pages 23-29. Protoplast fusion techniques for obtaining genetic recombination in *Brevibacterium flavum* are discussed by Kaneko et al. in Agric. Biol. Chem., 43 (5), 1007-1013 (1979). Protoplast fusion in Corynebacterium organisms is described by Katsumata et al. in published Japanese patent application No. 56-109587 (publication date Aug. 31, 1981). The process described by Katsumata et al. involves the use of penicillin and lysozyme. Canadian Pat. No. 1,105,859 also describes protoplast fusion as applied to Streptomyces.

Preparation of "co-integrate" plasmids for transformation of Streptomyces and *Escherichia coli* is described in U.S. Pat. Nos. 4,273,875 and 4,332,900. EPO application No. 058,889 (Katsumata and Furuya) describes plasmid cloning vectors for Corynebacterium.

The following microorganisms utilized in the invention are available from the permanent collection of the Northern Regional Research Laboratory, U.S. Department of Agriculture, Peoria, Ill., U.S.A.

A. *Corynebacterium glutamicum*, NRRL No. B-15340, a species containing the pSR1 plasmid described in Example 1.
B. *Bacillus subtilis*, NRRL No. B-15305, a species containing the pBD8 plasmid described in Example 2.
C. *Bacillus subtilis*, NRRL No. B-15306, a species containing the pBD10 plasmid described in Example 2.
D. *Bacillus subtilis*, NRRL No. B-15341, the species used for transformation in Example 4.
E. *Bacillus subtilis*, NRRL No. B-15342, a transformed species containing the pHY47 hybrid plasmid described in Example 4.
F. *Bacillus subtilis*, NRRL No. B-15307, a transformed species containing the pHY416 hybrid plasmid described in Example 4.
G. *Corynebacterium glutamicum*, NRRL No. B-15302, a transformed species containing the pHY416 plasmid described in Example 6.
H. *Corynebacterium glutamicum*, NRRL No. B-15303, a transformed species containing the pHY47 plasmid described in Example 6.
I. *Corynebacterium glutamicum*, NRRL No. B-15304, another transformed (NRRL B-15301) species also containing the pHY416 plasmid described in Example 6.
J. *Corynebacterium glutamicum*, NRRL No. B-15301, the species used for transformation in Example 7.

Additionally, the invention utilizes the following organisms already deposited with the American Type Culture Collection of Rockville, Md., U.S.A.

A. *Corynebacterium glutamicum*, ATCC No. 13059, the species used for transformation in Example 5.

DESCRIPTION OF THE DRAWINGS

FIG. 1 illustrates the scheme for constructing a chimeric plasmid and transforming various organisms.

FIG. 2 is a restriction endonuclease cleavage map for pSR1.

FIG. 3 is the procedure followed to construct the chimeric pSR1/pBD8 plasmid.

FIG. 4 is the procedure followed to construct the chimeric pSR1/pBD10 plasmid.

FIG. 5 is a restriction endonuclease cleavage map for pHY47.

FIG. 6 is a restriction endonuclease cleavage map for pHY416.

DESCRIPTION OF THE INVENTION

By this invention novel plasmids are provided that can be transformed and expressed in at least two different species of bacteria, both of said species being in different genera. The novel chimeric plasmids of the invention can be used to transform Corynebacterium organisms stably and at least one other species from a different genus, i.e., a non Corynebacterium organism. Many plasmids are of narrow host range and can only replicate and express their functions in bacteria of the same genus as the bacterium from which the plasmid was originally isolated. The invention provides chimeric plasmids that can replicate and express their functions in Corynebacterium and at least one organism from a different genus.

The strategy for constructing the chimeric plasmids is first to identify and isolate plasmid DNA from a Corynebacterium organism and then to join that DNA with plasmid DNA isolated from a bacteria of other genera (e.g., Bacillus, Staphylococcus, Streptococcus, Streptomyces, Escherichia, or Pseudomonas). It is most convenient if the plasmids employed in these constructions are relatively small and have molecular weights from about 2.0 to 20.0 Megadaltons ("Md"). Once a plasmid has been identified in a Corynebacterium organism its restriction endonuclease cleavage map is determined by standard techniques. In the early stages of designing such vectors, it is convenient if restriction endonucleases can be identified that cut the Corynebacterium plasmid at single sites so as to minimize the possibilities of deleting or inactivating essential polynucleotide sequences (such as the origin of replication and promoter sequences). If during the construction of chimeric plasmid it turns out that essential Corynebacterium sequences have been inactivated then a different chimeric plasmid can be constructed by utilizing a different restriction site(s) in the Corynebacterium plasmid.

In constructing a chimeric plasmid it is most convenient if the same restriction endonuclease is employed to digest both the Corynebacterium plasmid and the non-Corynebacterium plasmid so that the linearized sequences have cohesive ends. If a different restriction endonucleases are employed to cut the two plasmids then the ends of the plasmid DNA segments may need to be adjusted to permit ligation, e.g., there may be a need to remove unwanted tails, add homologous tails, etc. No matter what technique is used to generate the restriction fragments, the restriction endonuclease sites within the fragments will be preserved so that, after ligation and transformation, the plasmid can be isolated and subjected to restriction analysis as a method for confirming that the desired chimeric plasmid was constructed.

Following digestion, the plasmid restriction fragments from Corynebacterium and the non-Corynebacterium organism are mixed together and permitted to anneal followed by ligation with a suitable ligase, e.g., T4 DNA ligase. The particular ligases employed to ligate specific DNA segments are well known to those skilled in recombinant DNA techniques and include T4 DNA ligase and *Escherichia coli* DNA ligases. Following construction of the chimeric plasmid, the plasmid can be transformed into Corynebacterium as well as organisms from the genera providing the other restriction fragment(s) incorporated into the chimeric plasmid. Preferably the transformed organisms will be of the same species as the organisms providing the restriction fragment(s) although other species from the same genera as the donating parent species can be employed, e.g., for chimeric plasmids utilizing a restriction residue from *C. glutamicum*, other Corynebacterium species can be employed as hosts such as *C. hydrocarboclastus, C. parvum*, and *C. michiganense*. Bacteria closely related to Corynebacterium such as species of Brevibacterium i.e., *Brevibacterium flavum*, or *B. linens* and possibly streptomyces are also candidates. Similarly, if a restriction fragment from *Bacillus subtilis* is employed, suitable host organisms include Bacillus, Lactobacillus, Staphylococcus, Streptococcus, and Bifidobacterium.

The first step in Corynebacterium transformation is to convert the cells to a form in which exogenous DNA can be taken up by the cells. For example, converting cells to protoplasts could accomplish such a task. In this technique, a part or all of the rigid cell wall of the bacterium is removed so that the exogenous DNA entry can be facilitated with less hindrance. Protoplast formation is accomplished by growing Corynebacterium cells for several generations in the presence of from 0.1% to 2.1% of glycine followed by incubating the cells at from 30°-37° C. for from 0.5 to 4 hours in the presence of lysozyme and (subsequently) treating the cells with a water soluble chelating agent having at least two chelation sites. In addition to lysozyme lipase can also be employed although this is not necessary to prepare protoplasts. Suitable chelating agents include oxalic acid, nitrillotriacetic acid, ethylenediaminetetraacetic acid, and citric acid. The chelating agents are employed in the form of their water soluble alkali metal salts. During protoplast formation the cells are maintained in an osmotically stable (i.e., hypertonic) environment.

Stabilizing buffering agents can be prepared from sugars such as sucrose, ramnose, alcohols such as sorbitol, mannitol and high molecular weight polymers such as PEG and others.

The invention will be further described with reference to a specific embodiment (which is also described in more detail in the examples). With reference to FIG. 1, a procedure for constructing a particular Corynebacterium chimeric plasmid is depicted. Plasmid pBD10 from *Bacillus subtilis*, NRRL No. B-15306 is obtained. This plasmid (molecular weight about 4.4 Md) has antibiotic markers for resistance to kanamycin ("Km"), chloramphenicol ("Cm") and erythromycin ("Er"). The plasmid is reported to have a single Bcl I site contained within the gene for Em resistance but findings in this invention indicate that is not the case. A second plasmid (designated pSR1-molecular weight about 2.0 Md) was isolated from *Corynebacterium glutamicum* NRRL No. B-15340. The Corynebacterium plasmid was cryptic, i.e. the plasmid contained no common antibiotic resistance genes but did not contain a single Bcl I site. Following Bcl I digestion, the pBD10 and pSR1 plasmid residues were combined and ligated followed by transformation in to *Bacillus subtilis* NRRL-B-15341. Twenty-one colonies were obtained that were $Km^r$, $Cm^r$, and $Em^s$ of which 19 exhibited a molecular weight of only 3.2 to 3.4 Md. Two colonies NRRL B-15342, 15307 were obtained showing the same antibiotic pattern but having plasmids with apparent molecular weights closer to the anticipated molecular weight. The plasmid is one of these colonies was designated pHY47 and the plasmid from the other colony was designated pHY416. These plasmids were transformed into protoplasts from *C. glutamicum* ATCC 13059. The regenerated protoplasts yielded seven colonies from pHY47 that were $Km^r$ and $Cm^s$ but had a variable molecular weight and were unstable in the absence of Km. Two colonies were isolated from the pHY416 transformation that were $Km^r$ and $Cm^s$ and had approximately the same molecular weight as pHY416. The plasmid isolated from the pHY416 transformants were used to transform *B. subtilis* and the resulting transformants were $Km^r$, $Cm^r$, and $Em^s$. The same plasmid also was used to transform protoplasts from *C. glutamicum* NRRL No. B-15301 which was resistant to rifampycin ("Rif"). Three colonies were obtained that were all $Km^r$, $Cm^s$, and $Rif^r$ NRRL-B-15304.

The chimeric plasmids of the invention represent valuable intermediates for the development of improved host-vector systems. The process for introducing genetic information of interest into plasmids is well known in the art and such processes can be used to insert genes coding for various proteins, e.g., somatostatin, rat proinsulin, interferon, proteases, amino acid biosynthetic enzymes, and antibiotic biosynthetic enzymes. The usefulness of the chimeric plasmids of the invention should be contrasted with procedures for cloning genes into the well characterized *Escherichia coli* K-12 host-vector systems. The *E. coli* systems have the disadvantage that genes from some Gram-positive organisms, e.g., Bacillus, do not express well in the Gram-negative *E. coli* host. Likewise, plasmids from Gram-negative organisms are not easily maintained or are not maintained at all in Gram-positive hosts, and Gram-negative genetic information is either expressed poorly or not at all in Gram-positive hosts. This clearly argues for the advantage of a Gram-positive host-vector system particularly when cloning genes from Gram-positive organisms and suggests the usefulness of plasmids of the invention. Furthermore, since *C. glutamicum* is not a human pathogen as is *E. coli* it may prove useful for the cloning of particular genes of medical interest.

The invention can be utilized in several different ways. For example, microorganisms containing the chimeric Corynebacterium plasmids can be obtained from the depositories described above and the plasmids can be isolated from the cells, e.g., the cells can be lysed and the components of the cell wall can be separated from residual cellular components soluble in the lysate. The chimeric plasmid can then be isolated from the lysate. Procedures for accomplishing the above process are well known. For example, the host cells can be lysed by contacting the cells with a suitably hypotonic medium and/or the cells can be grown in the presence of glycine followed by exposing the cells to lysozyme and SDS. Separation of cell wall components can be accomplished simply by centrifugation at from 10,000 to 15,000 rpm, and the plasmid can be isolated from the lysate by cesium chloride/ethidium bromide density gradient centrifugation. The plasmid fraction can be separated from the chromosomal DNA and other components by use of a syringe.

Once isolated the chimeric plasmid can be subjected to restriction mapping followed by digesting with an appropriate set of restriction endonucleases. At this point the genetic information to be cloned can be inserted into the plasmid utilizing well known techniques. For example, the digested plasmid can be treated by well known techniques to make the ends cohesive with those of the DNA fragment containing the gene to be inserted. The plasmid residue is mixed with the DNA fragment carrying the gene of interest, and the plasmid and gene sequences are allowed to anneal, followed by ligation. Subsequently, the plasmid modified by insertion of the new polynucleotide sequence can be used to transform either a Corynebacterium species and/or bacteria from a second genus which contributed a plasmid fragment forming part of the chimeric plasmid. Transformation is accomplished by treating the host cells to render them competent followed by mixing the plasmid with the host cells and incubating the mixture to allow the plasmid to transform the host cells. Where the host cell is a Corynebacterium organism the cell is made competent by forming a protoplast as described above. Protoplasts are then transformed by mixing them with the chimeric plasmid carrying the inserted polynucleotide sequence while maintaining an osmotically stable environment. The mixture is incubated for a sufficient time to allow for transformation of the protoplast, e.g., from 5 to 90 mins at 37° C. The transformed protoplast is then incubated to allow regeneration of the cell wall. Incubation generally requires from 24 to 48 hours at 30° to 37° C. and is carried out in an osmotically stable environment as described above.

The invention can also be utilized by constructing the chimeric plasmid from plasmids obtained from Corynebacterium and from at least one other species of microorganism, e.g., a Bacillus species. The chimeric plasmid is constructed by digesting the Corynebacterium plasmid with a restriction endonuclease; digesting the plasmid obtained from the non-Corynebacterium organism with a restriction endonuclease; if necessary, treating one or both of the plasmid digests to make the ends of the fragments complementary, mixing the restriction endonuclease digestion products of the two plasmids and incubating in the presence of a ligase. The constructed chimeric plasmid can be isolated as described above and further digested with a restriction endonuclease to allow insertion of a foreign polynucleotide sequence coding for a desired protein, e.g., an antibiotic biosynthetic enzyme, amino acid biosynthetic enzyme, somatostatin, etc. The resulting chimeric plasmid carrying the inserted genetic information can then be used to transform a Corynebacterium protoplast or cells of a competent non-Corynebacterium organism from the genera (and preferably species) supplying one of the ligated plasmids.

Suitable Corynebacterium for use in the invention include, but are not limited to, the following species: *C. glutamicum, C. fasceans, C. hydrocarboclastus, C. michiganense, C. callunae, C. acetoacidophilum, C. parvum C. pseudotuberculosin, C. granulosum.*

Suitable non-Corynebacterium organisms for use in the invention include, but are not limited to, the following: Brevibacterium, Bifidobacterium, Bacillus, Peptostreptococcus, Staphylococcus, Clostridium, Streptococcus, Escherichia, Lactobacillus, Pseudomonas, Streptomyces.

EXAMPLE 1

Isolation and Characterization of Plasmids From *Corynebacterium glutamicum* NRRL No. B-15340

Cell lysis of *C. glutamicum* NRRL No. B-15340 was performed by a modification of the procedure described by Schiller et al., Antimicrobial Agents and Chemo. 18, 814 (1980) wherein log phase cultures (150–200 Klett units) were treated with 10 ug/ml of penicillin G at 37° C. for 2 hours. The cells were harvested and washed with Tris-HCl buffer (10 mM, pH 8.2). Subsequently, the cells (suspended in 0.3 ml 10 mM Tris-HCl in 0.5M sucrose at pH 8.2) were treated with 5/mg/ml of lysozyme at 37° C. for 1 hour with shaking and, following collection, the cells were treated with an aqueous solution of sodium dodecylsulfate at a final concentration of 1% in 10 mM Tris-HCl, 10 mM EDTA, pH 8.0 (i.e., "SDS") at room temperature for 15 minutes with occasional mixing to lyse the cells. Cellular debris and chromosomal DNA were removed by centrifugation for 15 min at 15,000 rpm and plasmids were then isolated from the cleared cell lysate by CsCl-EtBr density gradient centrifugation as described by Radloff et al., Proc. Natl. Acad. Sci. USA, 57, 1514 (1967). The lower band containing the plasmid DNA was collected by puncturing the centrifuge tube with a syringe needle. EtBr was removed by extraction with isopropanol saturated with 5M NaCl in TRIS-EDTA (10 mM:1 mM) buffer, pH 8.5.

Plasmid DNA was precipitated with 70% ethanol at $-20°$ C. over a period of 2 to 3 days. The precipitate was first washed with 70% EtOH and then with absolute EtOH. The precipitate was suspended in Tris buffer containing 10 ug/ml of RNase (i.e., ribonuclease-A from bovine pancreas). Agarose gel electrophoresis was carried out as described by P. Sharp et al., 1973 at 40 V for 14 hours, and indicated that *C. glutamicum* NRRL No. B-15340 contained at least one plasmid.

Further purification of plasmid DNA (necessary for restriction mapping) was achieved by subjecting the plasmid DNA to agarose gel electrophoresis through a single slot comb as described by Tabak and Flawell, Nucleic Acid Research, vol. 1 (No. 7, 2321–2332 (1978), i.e., small troughs were cut in the gel first in front of the plasmid band; the troughs were filled with hydroxyapatite suspended in electrophoresis buffer; and electrophoresis was continued for 1–2 hours until the plasmid DNA band had passed into the troughs. The hydroxyapatite-bound DNA was removed from a particular trough, laded on a Sephadex G-50 column and was eluted with 1M potassium phosphate buffer (pH 6.8). The plasmid DNA was precipitated with absolute ethanol at 0° C. Two separate DNA fractions were obtained indicating the presence of two plasmids for ATCC 19223.

The molecular weights of the *C. glutamicum* plasmids were determined relative to the standard migration patterns of publicly available plasmids, e.g., pBR322 (2.8 Md), pMB9 (3.6 Md), pSC101 (5.8 Md) and pRC1

(8.7 Md) during electrophoresis on an agarose gel. Based on this method the molecular weights of the two plasmids from *C. glutamicum* NRRL No. B-15340 appeared to be approximately 2.0 Md and 80 Md, respectively. The very large plasmid was not characterized.

Restriction mapping of the 2.0 Md *C. glutamicum* plasmid was conducted by digestion with restriction endonucleases obtained as commercial preparations from Bethesda Research Laboratories. Enzyme digestions were prepared in accordance with the conditions specified by the suppliers using at least a two-fold excess of endonuclease. The methodology employed was the double restriction endonuclease digestion described by Gryczan et al., J. Bacteriology, 134, 318 (1978), i.e., after incubation with the first restriction endonuclease, the sample was heated at 65° C. for 5 minutes and buffer components were added to bring the composition of the buffer as close as possible to that desired for the second restriction endonuclease. The average molecular weight of the fragments was determined by electrophoretic migration on an agarose gel and comparison with the migration of fragments from Hind III digestion of lambda phage DNA. The sum of the plasmid fragments was approximately 2.0 Md. This data was then used to construct the restriction map of FIG. 2. The sensitivity of the 2.0 Md plasmid to restriction endonucleases is as follows:

in LB broth with Chloramphenicol (Cm), Kanamycin (Km), and Erythromycin (Em). The concentration of all antibiotics was 5 ug/ml. The cells were collected by centrifugation at 6000 rpm for 20 minutes, washed with Tris buffer, sedimented, and suspended in 1/10 volume of a lysing buffer composed of 0.1M NaCl, 0.05M Tris and 25% sucrose, pH 7.5. Lysozyme was added at 0.5 mg/ml followed by incubation at 37° C. for 15 minutes and addition of 4.8 ml/20 ml of 5M NaCl; 1.2 ml/20 ml of 0.5M EDTA; and 26 ml/20 ml of 2% SDS 0.7M NaCl solution. Following gentle inversion the suspension was placed on ice for 18 hours at 4° C. followed by centrifugation at 15,000 rpm for 30 minutes. Cesium chloride-ethidium bromide dye buoyant density gradient centrifugation was employed to isolate the plasmids which were recovered and extracted three times with isopropanol to remove EtBr. The plasmids were precipitated with 70% EtOH; washed once with 90% EtOH; and washed once with absolute EtOH. The plasmids were placed in Tris buffer containing RNase and stored at $-20°$ C.

Two plasmids were identified and given the designations pBD-8 and pBD-10. Restriction analysis and molecular weight determinations for these plasmids were reported by Gryczan and Dubnau, "Construction and properties of chimeric plasmids in *B. subtilis,*" *Proc. Nat. Acad. Sci. USA*, 75, 1428–1432 (1978) and are set forth in the following table.

| Plasmid | Marker | M.W. ($\times 10$) | EcoR I | Hind III | Bgl II | Bamh I | Xba I | Bcl I |
| --- | --- | --- | --- | --- | --- | --- | --- | --- |
| pSR-1 | None | 2.0 | 0 | 2 | 1 | 1 | 0 | 1 |
| pBD-8 | Km, Cm, Sm | 6.0 | 1 | 1 | 1 | 1 | 1 | 0 |
| pBD-10 | Km, Cm, Em | 4.4 | 0 | 0 | 1 | 1 | 1 | 1 |

| Plasmid Sensitivities to Restriction Endonucleases | | | |
| --- | --- | --- | --- |
| # Cleavage Sites | | # Cleavage Sites | |
| Enzyme | 2.0 Md Plasmid | Enzyme | 2.0 Md Plasmid |
| Alu I | 2 | Xho I | 0 |
| EcoR I | 0 | Tac I | 2 |
| BamH I | 0 | Sst I | 2 |
| Hae III | 2 | Sst II | 1 |
| Hind III | 2 | Hinc II | 3 |
| Sal I | 0 | Bgl II | 1 |
| Hinf I | 3 | Bcl I | 1 |
| Ava I | 4 | Xba I | 0 |

In the remaining examples the 2.0 Md plasmid is generally referred to as "pSR1."

While plasmids can be isolated as described above, a preferable method is the sodium dodecylsulfate/NaCl technique described in Example 2. It should be noted that the 2.0 Md plasmid did not appear to contain genes for resistance to antibiotics, i.e., in this sense the plasmid was cryptic.

EXAMPLE 2

Isolation and Characterization of Plasmids From *Bacillus subtilis* NRRL No. B-15305, -15306

*B. subtilis* was grown in Luria Bertani broth, i.e., ("LB") at 37° C. with shaking. The composition of the LB medium was: Bacto-tryptone 10.0 g; yeast extract 5.0 g; NaCl 10.0 g and 1000 ml of $H_2O$. Plasmids were isolated by the sodium dodecylsulfate/NaCl method of Guerry et al., "General method for the isolation of plasmid deoxyribonucleic acid," J. Bacteriol., 116, 1064–1066 (1973) followed by dye-buoyant density centrifugation. This technique involves overnight culture Two deposits of the *Bacillus subtilis* strain have been made in connection with this application. *Bacillus subtilis,* NRRL No. B-15305, is known to contain the pBD8 plasmid while *Bacillus subtilis,* NRRL No. B-15306, is known to contain the pBD10 plasmid.

EXAMPLE 3

Construction and Characterization of Chimeric Plasmids

A. A chimeric plasmid was prepared from pSR1 and pBD8. The methods for digestion of plasmids and ligation of digested DNA were those reported by Gryczan et al. in the 1978 reference cited above, i.e., plasmid DNA was suspended in Tris buffer, admixed with Hind III, and incubated at 37° C. for 3 hours. The final concentration of the restriction endonuclease treated plasmid DNA in each reaction mixture was 15 ug/ml. The reaction mixture was heated for 15 minutes at 65° C. to inactivate the enzyme and ligation with T4 DNA ligase was carried out at 10° C. for 20 hours.

B. The pSR1/pBD10 chimeric plasmid was prepared as described by Gryczan et al. by suspending plasmid DNA in Tris buffer followed by digestion with BclI at 50° C. for 3 hours. The reaction mixture was heated at 70° C. for 30 minutes to inactivate the enzyme followed by ligation at 10° C. for 20 hours with T4 DNA ligase.

The pSR1 plasmid has two Hind III sites but does not appear to contain markers for common antibiotics. The pBD8 plasmid contains markers for $Km^r$, $Cm^r$ and $Sm^r$. However, the $Sm^r$ site also contains a single Hind III site and is inactivated during digestion. Transformants containing this chimeric plasmid can be selected for resistance to Km and Cm and sensitivity to Sm although, as discussed below, the Cm gene is apparently not expressed in transformed *C. glutamicum* hosts.

The pSR1 plasmid has a single Bcl I site and pBD10 has a single Bcl I site. The pBD10 plasmid contains markers for Km$^r$, CM$^r$ and Em$^r$. However, the Em$^r$ gene contains the Bcl I site and is inactivated during digestion. Therefore, transformants, in principle, can be selected for resistance to Km and Cm but sensitivity to Em; however, as indicated above, the Cm gene is apparently not expressed in regenerated *C. glutamicum* protoplasts.

The schemes for construction of the chimeric pSR1/pBD8 and pSR1/pBD10 plasmids are set forth in FIGS. 3 and 4, respectively.

EXAMPLE 4

Transformation of *Bacillus subtilis* NRRL No. B-15341

Competent cells of *B. subtilis* NRRL No. B-15341 were prepared as described by Gryczan et al., "Construction and properties of chimeric plasmids in *B. subtilis*," Proc. Nat. Acad. Sci., USA 75, 1428–1432 (1978); i.e., after culturing overnight in SPI medium SPI medium:
  0.02% Casamino acids
  0.1% Diflo Yeast Extract
  0.5% Glucose
  0.2% $(NH_4)_2SO_4$
  1.4% $K_2HPO_4$
  0.6% $KH_2PO_4$
  0.1% Sodium citrate
  0.02% $Mg_2SO_4 7H_2O$ at 30° C., the cells were diluted with fresh SpI medium to 10–15 Klett units and incubated at 37° C. until the early stationary phase was obtained. The medium was diluted ten fold into SPII medium (SPI medium plus $5 \times 10^{-4}M$ $CaCl_2$ and $2.5 \times 10^{-3}M$ $MgCl_2$) followed by incubation at 37° C. for 90 minutes. The cells were collected at 0°–4° C. by centrifugation and resuspended in 0.1 volume of the same supernatant.

The cells were transformed with the chimeric pSR1/pBD8 and pSR/1/pBD10 plasmids prepared as in Example 3. The method employed is described by Gryczan et al. (supra). In the transforming medium the concentration of chimeric plasmid was 15 ug/ml. The transformation medium was incubated at 37° C. for 20 minutes. Transformants were selected using drug plates by the overlay method. As a control, cells were also transformed with just pBD8 or pBD10.

Transformation results are presented in the following table.

| Plasmid | Selected Marker | Transformants per g of Plasmid DNA |
|---|---|---|
| pBD8 | Km, Cm, Sm | $6.7 \times 10^2$ |
| pSR1/pBD8 | Km, Cm | $4.0 \times 10$ |
| pBD10 | Km, Cm, Em | $3.7 \times 10^2$ |
| pSR1/pBD10 | Km, Cm | $1.3 \times 10^2$ |

The transformants were grown for 1 day on LB medium and were screened for drug resistance and the presence of plasmid DNA. Plasmid DNA was isolated by the SDS/NaCl technique (Example 2) followed by purification over agarose gel (Example 1) and restriction mapping.

Analysis of the plasmids indicated that all ten pSR1/pBD8 transformants contained a 5.8 Md plasmid which is considerably smaller than the 7.8–8.0 Md plasmid expected. These clones were all Km$^r$, Cm$^r$ and Sm$^r$, perhaps indicating splitting out of the pSR1 fragment. The pSR1/pBD10 transformants yielded two clones containing a plasmid with an apparent molecular weight of 5.2–5.5 Md which approximates the 6.4 Md plasmid expected. Sixteen of the remaining clones contained plasmids ranging from 3.7 to 3.9 Md and appeared to be resistant to Km, Cm and Em, i.e., the improper antibiotic pattern perhaps indicating splitting out of the pSR1 fragment.

The two 5.2–5.5 plasmids from pSR1/pBD10 (designated respectively as pHY47 and pHY416) were subjected to restriction mapping with the following results:

| Plasmid | Fragment Size Digested ($\times$ 10 dal.) | | |
|---|---|---|---|
| | Bcl I | BamH I | Bgl II |
| pHY47 | 1.86(2) | 6.17(1) | 1.86(2) |
| | 3.94 | | 3.94 |
| pHY416 | 1.86(2) | 6.17(1) | 2.02(2) |
| | 3.394 | | 3.63 |
| pBD10 | 3.85(2) | 4.4(1) | 4.52(1) |
| pSR1 | 1.88(1) | — | — |

( ) = number of restriction enzyme sites detected.

It is apparent that digestion with Bcl I yielded 2 fragments with molecular weights approximately equal to those of pBD10 and pSR1, indicating that the original ligation points were preserved in the chimeric plasmid. The original pBD10 and pSR1 have unique single sites for Bgl II. Therefore, it was expected that the chimeric plasmid would have two Bgl II sites. Bgl II digestion resulted in 2 fragments as expected but the molecular weights of the resulting fragments from the two plasmis were different indicating perhaps a difference in orientation of the plasmid DNAs during ligation.

Restriction maps for pHY47 and pHY416 are set forth in FIGS. 5 and 6, respectively. The *B. subtilis* species containing the pHY47 and pHY416 plasmids have been deposited with the Northern Regional Research Laboratory in Peoria, Ill., and bear (respectively) accession numbers NRRL B-15342 and B-15307.

EXAMPLE 5

Preparation of Protoplasts From *Corynebacterium glutamicum*

Protoplasts from *C. glutamicum* ATCC 13059 were prepared by the following method. Cells were cultured overnight in LB broth at concentrations of from 0.7 to 2.1% of glycine. It was found that 2.1% glycine gave the most efficient protoplast formation. The cells were harvested and washed with Tris-HCl buffer (10 mM, pH 8) and suspended in Tris-Sucrose TSSCM buffer (Tris 10 mM, sucrose 0.5M, NaCl 1.0 mM, $CaCl_2$ 0.5 mM and $MgCl_2$ 25 mM) at pH 8. A 0.5 ml cell suspension was prepared to which 0.5 ml of lysozyme in the above buffer (5 mg/ml) was added followed by mild shaking at 37° C. for 3 hours. EDTA (100 mM) was added followed by gentle shaking at 37° C. for from 10 to 15 minutes.

The extent of protoplasting was followed by plating the cells on LB agar using distilled water as a diluent and comparing the number of colonies formed with those formed when cells were plated on DM3 medium (Chang and Cohen, 1979, Mol. Gen. Genet. 168, 111–115).

DM 3 Regeneration Agar
(Sterile solutions)
4% Agar-200 ml
1M Sodium succinate pH 7.3-500 ml
5% Difco casamino acids-100 ml
10% Difco yeast extract-50 ml
3.5% $K_2HPO_4$ and 1.5% $KH_2$-$PO_4$-100 ml
20% glucose-25 ml
1M $MgCl_2$-20 ml
2% BSA (filter sterilized)-5 ml
Gelatin 5 gm/li
Trace elements:
   $FeSo_4$, $7H_2O$—5 ug/li
   $MnSO_4$, $4H_2O$—5 ug/li
   $ZnSo_4$, $7H_2O$—2 ug/li
using Tris-sucrose buffer (pH 6.5) as diluent. An increase in plating efficiency as a result of exposure of the protoplasts to an osmotically stable environment rather than distilled water was used as an indicator of protoplast formation. The frequency of regeneration of the protoplasts was followed by diluting the protoplasts in distilled water or sucrose buffer (pH 6.5) and plating on LB or DM3 plates, respectively.

The efficiency of regeneration of protoplasts was found to be dependent on the glycine concentration in the original growth medium. At 0.7% glycine concentration, there was over 99% protoplast formation and very high (100%) regeneration of the protoplasts. At higher glycine concentrations, i.e., 2.1%, in the original growth medium the regeneration of protoplasts was only 30-35%. At a glycine concentration of 1.4% in the growth medium, 60% of the protoplasts regenerated.

Electron microscopy indicated that more cell wall was removed during the protoplasting of cells grown in 2.1% as compared to lower concentrations of glycine. A more complete removal of the cell wall is desirable to remove any hindrance to uptake of plasmid DNA by the cell. A concentration of 2.1% glycine in the growth medium was therefore chosen for the preparation of *C. glutamicum* protoplasts for transformation.

EXAMPLE 6

Transformation of *C. glutamicum* Protoplasts

The transformation of procedure employed was similar to a procedure reported for Streptomyces (Bibb et al., Transformation of plasmid DNA into Streptomyces at a high frequency. Nature, 274, 398-400) except polyethylene glycol 8000 (Mol. Wt. 8000, Sigma Chemical Co., St. Louis, MO) was used rather than polyethylene glycol 1000.

Protoplasts (prepared as in Example 5) were transformed with the pHY47 and pHY416 chimeric plasmids isolated as described in Example 4. The transformation procedure was the same in both cases and, as a control, protoplasts were subjected to the same procedure but in the absence of the plasmid DNA.

A 0.6 ml suspension of protoplasts was pelleted in a bench top centrifuge and the supernatant was discarded followed by gentle resuspension of the cells in the remaining supernatant. This suspension was gently mixed with plasmid DNA (10 ug/17 ul buffer) and 0.5 ml of 40% PEG 8000 in water was added and, after about one minute, a further 0.5 ml of 20% PEG 8000 in water was added and mixed for three minutes at room temperature. About 4 ml of SMM buffer (0.5M sucrose, 0.02M maleate, 0.02M Magnesium chloride, pH 6.5) was added with gentle mixing followed by centrifugation for 15 minutes at ½ speed in a bench top centrifuge. Enough SMM buffer was added to bring the volume to 200 ul and the pellet was resuspended.

From the final 200 ul suspension, 50 ul was plated directly onto DM3 plates and incubated at 37° C. for 72 hours to allow for regeneration of the protoplasts. Another 50 ul was serially diluted with 5 ml buffer and plated onto DM3 plates followed by incubation at 37° C. for 72 hours. 100 ul of suspension was maintained at room temperature for 60 minutes and was plated directly onto DM3 plates containing 5 ug/ml of either Km, Cm or Km/CM. In the Km/Cm plates 5 ug/ml of both antibiotics were employed. The additional 60 minute period prior to plating onto antibiotic plates has been reported to increase transformation frequency in *Bacillus subtilis*, i.e., see Chang and Cohen, "High frequency transformation of *Bacillus subtilis* protoplasts by plasmid DNAs," Mol. Gen. Genet., 168, 111-115 (1979). Transformations of *C. glutamicum* containing either pHY47 or pHY416 would be expected to be Km and Cm resistant. The protoplasts employed did not contain plasmids prior to transformation and did not exhibit resistance to Km or Cm.

Approximately 60-70% of the original protoplasts were recovered at the end of transformation. No transformants resistant to both Km and Cm were observed on DM3-Km/Cm plates after 72 hours at 37° C. The *C. glutamicum* protoplasts exposed to plasmid DNA and regenerated for 72 hrs. at 37° C. on DM3 plates containing no Km or Cm were replica plated onto LB plates containing different concentrations of either Km or Cm. The protoplasts transformed with pHY47 produced 7 transformants which were resistant to 10 ug/ml of Km. Protoplasts transformed with pHY416 produced 2 transformants which were resistant to 10 ug/ml Km. None of these *C. glutamicum* pHY47 or pHY416 transformants were Cm resistant indicating that the Cm resistance gene was either not expressed or deleted upon transformation into *C. glutamicum*. All 9 *C. glutamicum* transformants that were Km resistant and Cm sensitive contained plasmids of the same molecular weight (determined as described above) as the respective plasmid used for the original transformation indicating no possible major deletion had occurred upon transformation into *C. glutamicum*. To determine if the Cm resistance gene was present but not expressed in *C. glutamicum*, plasmid was isolated from *C. glutamicum* transformants and used to transform *B. subtilis*. All *B. subtilis* cells transformed with pHY416 isolated from *C. glutamicum* transformants were both Km and Cm resistant proving that the Cm resistance gene was retained but not expressed in *C. glutamicum* transformed with pHY416.

The transformation frequency for *B. subtilis* with pHY416 propagated in *C. glutamicum* was low, e.g., about 0.5 transformants per ug plasmid DNA. In contrast the transformation frequency for *B. subtilis* with pHY416 propagated in *B. subtilis* was $1-2\times10^5$ per ug of plasmid DNA. The lower transformation frequency with pHY416 isolated from *C. glutamicum* may be due to modifications of the plasmid in *C. glutamicum*.

The stability of both pHY416 and pHY47 plasmids in the *C. glutamicum* protoplasts was investigated by growing the transformants without Km selection pressure. The results indicate that pHY416 was stable and retained in *C. glutamicum* as compared to pHY47 which was rapidly lost without Km selection.

Sample cultures of the *C. glutamicum* transformants containing pHY47 and pHY416 have been deposited and bear (NRRL) accession numbers B-15302 (containing plasmid pHY416) and B-15303 (containing plasmid pHY47).

EXAMPLE 7

Protoplasts from *C. glutamicum* were prepared as described above. The particular strain employed was resistant to rifampycin, i.e., Rif® and has the deposit accession number NRRL B-15301. Transformation of *C. glutamicum* NRRL B-15301 produced three transformants that were Km and Rif resistant although the transformants were again Cm sensitive. This transformant bears the NRRL accession number B-15304.

I claim:

1. An essentially pure plasmid pSR1, derived from a coryneform microorganism, in an isolated form suitable for use as a cloning vector for expressing foreign and native genes in coryneform microorganisms, the plasmid having a molecular weight of about 2 megadaltons and having the following cleavage sites for restriction endonucleases:

| Enzyme | # of Cleavage Sites |
|---|---|
| EcoR I | 0 |
| Hind II | 2 |
| Bgl II | 1 |
| Bamh I | 1 |
| Xba I | 0 |
| Bcl I | 1. |

2. The plasmid according to claim 1 which is isolated from a Corynebacterium microorganism having the identifying characteristics of NRRL Deposit No. B-15340.

3. An essentially pure plasmid pBD8 derived from a *Bacillus subtilus* microorganism, in an isolated form suitable for use as a cloning vector for expressing foreign and native genes in Bacillus microorganisms, the plasmid having a molecular weight of about 6 megadaltons and having the following cleavage sites for restriction endonucleases:

| Enzyme | # of Cleavage Sites |
|---|---|
| ECoR I | 1 |
| Hind II | 1 |
| Bgl II | 1 |
| Bamh I | 1 |
| Xba I | 1 |
| Bcl II | 0. |

4. The plasmid according to claim 3 which is isolated from a Bacillus microorganism having all the identifying characteristics of NRRL Deposit No. B-15305.

5. An essentially pure plasmid pBD10 derived from a *Bacillus subtilus* microorganism, in an isolated form suitable for use as a cloning vector for expressing foreign and native genes in Bacillus microorganisms, the plasmid having a molecular weight of about 6 megadaltons and having the following cleavage sites for restriction endonucleases:

| Enzyme | # of Cleavage Sites |
|---|---|
| EcoR I | 0 |
| Hind III | 0 |
| Bgl II | 1 |
| Bamh I | 1 |
| Xba I | 1 |
| Bcl I | 1. |

6. The plasmid according to claim 5 which is isolated from a Bacillus microorganism having all the identifying characteristics of NRRL Deposit No. B-15306.

7. A chimeric plasmid pHY416 of about 5 megadaltons molecular weight prepared by isolating a first plasmid of about 2 megadaltons molecular weight from a Corynebacterium microorganism and a second plasmid of about 4 megadaltons from a Bacillus microorganism, cleaving the plasmids with a restriction endonuclease, and ligating the cleaved plasmids to one another to produce a chimeric plasmid having the following cleavage sites for restriction endonucleases:

| Enzyme | # of Cleavage Sites |
|---|---|
| Bcl I | 2 |
| BamH I | 1 |
| Bgl II | 2. |

* * * * *